United States Patent
Herold et al.

(10) Patent No.: US 7,795,253 B2
(45) Date of Patent: *Sep. 14, 2010

(54) CONDENSED IMIDAZOLE DERIVATIVES AS AROMATASE INHIBITORS

(75) Inventors: Peter Herold, Allschwil (CH); Robert Mah, Allschwil (CH); Vincenzo Tschinke, Allschwil (CH); Aleksandar Stojanovic, Allschwil (CH); Christiane Marti, Allschwil (CH); Stefan Stutz, Allschwil (CH)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/226,209

(22) PCT Filed: Apr. 12, 2007

(86) PCT No.: PCT/EP2007/053586

§ 371 (c)(1),
(2), (4) Date: Oct. 10, 2008

(87) PCT Pub. No.: WO2007/116100

PCT Pub. Date: Oct. 18, 2007

(65) Prior Publication Data

US 2009/0048241 A1    Feb. 19, 2009

(30) Foreign Application Priority Data

Apr. 12, 2006 (CH) .................. 0617/06

(51) Int. Cl.
*C07D 498/04* (2006.01)
*A61K 31/5365* (2006.01)

(52) U.S. Cl. .................. 514/230.5; 544/105
(58) Field of Classification Search .......... 544/105; 514/230.5
See application file for complete search history.

(56) References Cited

U.S. PATENT DOCUMENTS 4,369,309 A    1/1983    Eto et al.
4,450,109 A    5/1984    Eto et al.
2009/0012068 A1    1/2009    Herold et al.

FOREIGN PATENT DOCUMENTS

| JP | 63145286 A * | 6/1988 |
| WO | WO 9700257 A1 * | 1/1997 |
| WO | 2005/118557 | 12/2005 |
| WO | 2005/118581 | 12/2005 |

OTHER PUBLICATIONS

International Search Report dated Jul. 9, 2007 in the International (PCT) Application PCT/EP2007/053586 of which the present application is the U.S. National Stage.
Written Opinion dated Jul. 9, 2007 in the International (PCT) Application PCT/EP2007/053586 of which the present application is the U.S. National Stage.
Database WPI, Derwent Publications Ltd., AN 1988-209105, XP002439664 & JP 63 145286 A, Jun. 17, 1988.
Office Action dated Jul. 10, 2009 and response thereto filed Aug. 10, 2009 in related U.S. Appl. No. 12/223,789.
Office Action dated Sep. 29, 2009 and response thereto filed Dec. 29, 2009 in related U.S. Appl. No. 12/223,789.
Office Action dated Jan. 26, 2010 and response thereto filed Apr. 26, 2010 in related U.S. Appl. No. 12/223,789.

* cited by examiner

*Primary Examiner*—Kahsay T Habte
(74) *Attorney, Agent, or Firm*—Wenderoth, Lind & Ponack, L.L.P.

(57) ABSTRACT

The application relates to novel heterocyclic compounds of the general formula (I) and salts, preferably pharmaceutically acceptable salts, thereof, in which R, $R^1$, $R^2$, $R^3$, Q, m and n have the meanings explained in detail in the description, and * designates an asymmetric carbon atom, a process for their preparation and the use of these compounds as medicaments, in particular as aromatase inhibitors.

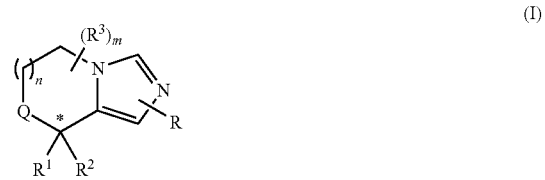

7 Claims, No Drawings

CONDENSED IMIDAZOLE DERIVATIVES AS AROMATASE INHIBITORS

FIELD OF THE INVENTION

The invention relates to novel heterocyclic compounds, processes for preparing the compounds, pharmaceutical products containing them, and their use as active pharmaceutical ingredients, especially as aromatase inhibitors.

DETAILED DESCRIPTION OF THE INVENTION

The present invention relates firstly to compounds of the general formula

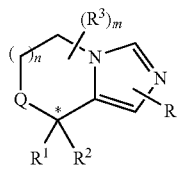

in which
R is deuterium, halogen, or hydrogen;
$R^1$ is aryl-$C_0$-$C_4$-alkyl or heterocyclyl-$C_0$-$C_4$-alkyl, which radicals may be substituted by 1-4 $C_1$-$C_8$ alkoxy, $C_1$-$C_8$ alkoxycarbonyl, $C_1$-$C_8$ alkyl, $C_0$-$C_8$ alkylcarbonyl, $C_1$-$C_8$ alkylsulphonyl, optionally substituted aryl, aryl-$C_0$-$C_4$ alkoxycarbonyl, cyano, halogen, optionally substituted heterocyclyl, hydroxy, nitro, oxide, oxo, tri-$C_1$-$C_4$ alkylsilyl, trifluoromethoxy or trifluoromethyl;
$R^2$ is a) deuterium, halogen, hydroxy, cyano or hydrogen; or
b) $C_2$-$C_8$ alkenyl, $C_2$-$C_8$ alkynyl, $C_1$-$C_8$ alkoxy, $C_1$-$C_4$ alkoxycarbonyl-$C_1$-$C_4$ alkyl, $C_1$-$C_8$ alkyl, $C_0$-$C_4$ alkylcarbonyl, aryl-$C_0$-$C_4$ alkyl, carboxy-$C_1$-$C_4$ alkyl, $C_3$-$C_8$ cycloalkyl or heterocyclyl-$C_0$-$C_4$ alkyl, which radicals may be substituted by 1-4 $C_1$-$C_8$ alkoxy, $C_1$-$C_8$ alkoxycarbonyl, $C_1$-$C_8$ alkyl, $C_0$-$C_8$ alkylcarbonyl, $C_1$-$C_8$ alkylsulphonyl, optionally substituted aryl, aryl-$C_0$-$C_4$ alkoxycarbonyl, cyano, halogen, optionally substituted heterocyclyl, hydroxy, nitro, oxide, oxo, tri-$C_1$-$C_4$ alkylsilyl, trifluoromethoxy or trifluoromethyl;
$R^3$ is $C_1$-$C_8$ alkyl;
Q is oxygen or sulphur;
m is a number 0, 1 or 2;
n is a number 0, 1 or 2;

and salts, preferably pharmaceutically acceptable salts, thereof where
$R^1$ is not $C_1$-$C_8$ alkyl-substituted aryl if $R^2$ is hydrogen.

A compound of formula (I) is to be understood as a compound having a specific configuration around the designated asymmetric carbon atom labelled "*". If a synthesis method is used which leads to racemic compounds, the racemate resolution is carried out in accordance with conventional methods, such as via a chiral HPLC column. Compounds of the formula (I) as described in the present invention exhibit a pronounced aromatase inhibitory activity. The aforementioned activity can, readily and as described below, be determined by using a commercial Cyp19 enzyme inhibition kit, preferably the Cyp19/methoxy-4-trifluoromethyl-coumarin (MFC) high throughput inhibition kit (Becton Dickinson Biosciences, San Jose, Calif., USA) as described hereafter. In the above-mentioned inhibition kit, compounds of the formula (I) show an inhibiting activity which is at least 10 times higher, but preferably 20 times higher, or more preferably 40 times higher, than the substances of the formula (I) with the opposite configuration around the asymmetric carbon atom labelled "*". A higher inhibiting activity corresponds to a lower $IC_{50}$ value.

The term aryl stands for a mono-, bi- or tricyclic aromatic hydrocarbon complying with the Hückel rule which generally comprises 6-14, preferably 6-10, carbon atoms and is for example phenyl, naphthyl, e.g. 1- or 2-naphthyl or anthracenyl. Aryl having 6-10 carbon atoms, in particular phenyl or 1- or 2-naphthyl, is preferred. The stated radicals may be unsubstituted or substituted one or more times, e.g. once or twice, in which case the substituent may be in any position, e.g. in the o, m or p position of the phenyl radical or in the 3 or 4 position of the 1- or 2-naphthyl radical, and there may also be a plurality of identical or different substituents present. Examples of substituents on aryl radicals or the preferred phenyl or naphthyl radicals are: $C_1$-$C_8$ alkoxy, $C_1$-$C_8$ alkoxycarbonyl, $C_1$-$C_8$ alkyl, $C_0$-$C_8$ alkylcarbonyl, $C_1$-$C_8$ alkylsulphonyl, optionally substituted aryl, aryl-$C_0$-$C_4$ alkoxycarbonyl, cyano, halogen, optionally substituted heterocyclyl, hydroxy, nitro, tri-$C_1$-$C_4$ alkylsilyl, trifluoromethoxy or trifluoromethyl.

Aryl-$C_0$-$C_4$ alkyl is for example phenyl, naphthyl or benzyl.

The term heterocyclyl stands for a saturated, partially saturated or unsaturated, 4-8-membered, particularly preferably 5-membered, monocyclic ring system, for a saturated, partially saturated or unsaturated, 7-12-membered, particularly preferably 9-10-membered, bicyclic ring system and also for a partially saturated or unsaturated, 9-12-membered tricyclic ring system which comprises an N, O or S atom in at least one of the rings, it being possible for an additional N, O or S atom to be present in one ring. Said radicals may be unsubstituted or substituted one or more times, e.g. once or twice, and there may also be a plurality of identical or different substituents present. Examples of substituents on heterocyclyl radicals are: $C_1$-$C_8$ alkoxy, $C_1$-$C_8$ alkoxycarbonyl, $C_1$-$C_8$ alkyl, $C_0$-$C_8$ alkylcarbonyl, $C_1$-$C_8$ alkylsulphonyl, optionally substituted aryl, aryl-$C_0$-$C_4$ alkoxycarbonyl, cyano, halogen, optionally substituted heterocyclyl, hydroxy, nitro, oxide, oxo, tri-$C_1$-$C_4$ alkylsilyl, trifluoromethoxy or trifluoromethyl.

Saturated heterocyclyl-$C_0$-$C_4$ alkyl is for example azepanyl, azetidinyl, aziridinyl, 3,4-dihydroxy-pyrrolidinyl, 2,6-dimethylmorpholinyl, 3,5-dimethylmorpholinyl, dioxanyl, [1,4]dioxepanyl, dioxolanyl, 4,4-dioxothiomorpholinyl, dithianyl, dithiolanyl, 2-hydroxymethylpyrrolidinyl, 4-hydroxypiperidinyl, 3-hydroxypyrrolidinyl, 4-methylpiperazinyl, 1-methylpiperidinyl, 1-methylpyrrolidinyl, morpholinyl, oxathianyl, oxepanyl, 2-oxo-azepanyl, 2-oxo-imidazolidinyl, 2-oxo-oxazolidinyl, 2-oxo-piperidinyl, 4-oxo-piperidinyl, 2-oxo-pyrrolidinyl, 2-oxo-tetrahydropyrimidinyl, 4-oxo-thiomorpholinyl, piperazinyl, piperidinyl, pyrrolidinyl, tetrahydrofuranyl, tetrahydropyranyl, tetrahydrothiophenyl, tetrahydrothiopyranyl, thiepanyl or thiomorpholinyl.

Partially saturated bicyclic heterocyclyl-$C_0$-$C_4$ alkyl is for example 3,4-dihydro-2H-benzo[1,4]oxazinyl, 4,5,6,7-tetrahydrobenzofuranyl or 4,5,6,7-tetrahydrobenzothiazolyl.

Unsaturated bicyclic heterocyclyl-$C_0$-$C_4$ alkyl is for example benzofuranyl, benzoimidazolyl, benzo[d]isothiazolyl, benzo[d]isoxazolyl, benzo[b]thiophen-yl, quinolinyl, imidazo[1,5-a]pyridinyl, indazolyl, indolyl or isoquinolinyl.

Unsaturated monocyclic heterocyclyl-$C_0$-$C_4$ alkyl is for example imidazolyl, oxazolyl, pyridyl, pyrrolyl, tetrazolyl, thiazolyl or thiophenyl.

$C_2$-$C_8$ alkenyl is for example ethenyl, propenyl, isopropenyl, butenyl, isobutenyl, secondary butenyl, tertiary butenyl, or a pentynyl, hexenyl or heptenyl group.

$C_2$-$C_8$ alkynyl is for example ethynyl, propynyl, butynyl, or a pentynyl, hexynyl or heptynyl group.

$C_1$-$C_8$ alkoxy is for example $C_1$-$C_5$ alkoxy such as methoxy, ethoxy, propoxy, isopropoxy, butoxy, isobutoxy, secondary butoxy, tertiary butoxy or pentoxy, but may also be a hexoxy or heptoxy group.

$C_1$-$C_8$ alkoxycarbonyl is preferably $C_1$-$C_4$ alkoxycarbonyl such as methoxycarbonyl, ethoxycarbonyl, propoxycarbonyl, isopropoxycarbonyl, butoxycarbonyl, isobutoxycarbonyl, secondary butoxycarbonyl or tertiary butoxycarbonyl.

$C_1$-$C_4$ alkoxycarbonyl-$C_1$-$C_4$ alkyl is for example methoxycarbonylmethyl or ethoxycarbonylmethyl, 2-methoxycarbonylethyl or 2-ethoxycarbonylethyl, 3-methoxycarbonylpropyl or 3-ethoxycarbonylpropyl or 4-ethoxycarbonylbutyl.

$C_1$-$C_8$ alkyl may be straight-chain or branched and/or bridged and is for example methyl, ethyl, propyl, isopropyl, butyl, isobutyl, secondary butyl, tertiary butyl, or a pentyl, hexyl or heptyl group.

$C_0$-$C_8$ alkylcarbonyl or preferably $C_0$-$C_4$ alkylcarbonyl is for example formyl, acetyl, propionyl, propylcarbonyl, isopropylcarbonyl, butylcarbonyl, isobutylcarbonyl, secondary butylcarbonyl or tertiary butylcarbonyl.

Carboxy-$C_1$-$C_4$ alkyl is for example carboxymethyl, 2-carboxyethyl, 2- or 3-carboxypropyl, 2-carboxy-2-methylpropyl, 2-carboxy-2-ethylbutyl, or 4-carboxybutyl, in particular carboxymethyl.

$C_3$-$C_8$ cycloalkyl is preferably 3-, 5- or 6-membered cycloalkyl, such as cyclopropyl, cyclopentyl, cyclohexyl.

Halogen is for example fluorine, chlorine, bromine or iodine.

The compound groups mentioned below are not to be regarded as closed; on the contrary, parts of these compound groups may be replaced by one another or by the definitions given above, or be omitted, in a meaningful way, e.g. to replace general by more specific definitions. The definitions mentioned apply within the scope of general chemical principles such as, for example, the usual valencies of atoms.

R is preferably deuterium or hydrogen.

$R^1$ is preferably aryl, very particularly preferably mono-, di- or tri-substituted phenyl or mono-, di- or tri-substituted naphthyl, or heterocyclyl, very particularly preferably optionally mono-, di- or tri-substituted benzofuranyl, benzo[b]thiophenyl, benzoimidazolyl, benzo[d]isothiazolyl, benzo[d]isoxazolyl, benzo[b]thiophenyl, imidazolyl, indazolyl, indolyl, oxazolyl, pyridyl, pyrrolyl, thiazolyl or thiophenyl.

$R^2$ is preferably $C_1$-$C_8$ alkoxy, hydroxy, $C_1$-$C_8$ alkyl, optionally substituted aryl-$C_0$-$C_4$ alkyl, deuterium, halogen, cyano or hydrogen.

$R^3$ is preferably $C_1$-$C_4$ alkyl.

n is preferably a number 0 or 1. n is particularly preferably the number 1.

Preferred substituents for aryl or heterocyclyl are $C_1$-$C_8$ alkoxy, $C_1$-$C_8$ alkyl, $C_1$-$C_8$ alkylcarbonyl, $C_1$-$C_8$ alkylsulphonyl, optionally substituted aryl, cyano, halogen, optionally substituted heterocyclyl, nitro, oxide, trifluoromethyl, trifluoromethoxy or trimethylsilanyl. Very particularly preferred substituents for aryl or heterocyclyl are acetyl, bromine, chlorine, cyano, fluorine, methanesulphonyl, methoxy, nitro, oxazolyl, oxide, optionally substituted phenyl, optionally substituted tetrazolyl, optionally substituted thiazolyl or optionally substituted thiophenyl.

It is likewise preferred for $R^1$ to be a mono-, di - or tri-substituted unsaturated heterocyclyl substituent, where the substituents are preferably selected from the group consisting of $C_1$-$C_8$ alkyl, $C_1$-$C_8$ alkoxy, $C_1$-$C_8$ alkoxycarbonyl, $C_0$-$C_8$ alkylcarbonyl, $C_1$-$C_8$ alkylsulphonyl, optionally substituted aryl, aryl-$C_0$-$C_4$ alkoxycarbonyl, cyano, halogen, optionally substituted heterocyclyl, hydroxy, nitro, oxide, oxo, tri-$C_1$-$C_4$ alkylsilyl, trifluoromethoxy and trifluoromethyl.

Compounds having a second asymmetric carbon atom can exist in the form of optically pure diastereomers, mixtures of diastereomers, diastereomeric racemates, mixtures of diastereomeric racemates, or meso compounds. The invention embraces all these forms. Mixtures of, diastereomers, diastereomeric racemates, or mixtures of diastereomeric racemates can be fractionated by conventional methods, such as by racemate resolution, column chromatography, thin-layer chromatography, HPLC and the like.

The expression "pharmaceutically acceptable salts" embraces salts with organic or inorganic acids, such as hydrochloric acid, hydrobromic acid, nitric acid, sulphuric acid, phosphoric acid, citric acid, formic acid, maleic acid, acetic acid, succinic acid, tartaric acid, methane-sulphonic acid, p-toluenesulphonic acid and the like. Salts of compounds containing salt-forming groups are, in particular, acid addition salts, salts with bases or else, if appropriate, if two or more salt-forming groups are present, are mixed salts or inner salts.

The compounds of the formula (I) can be prepared in an analogous manner to the preparation processes disclosed per se in the literature by JP63145286, followed by separation into the antipodes with regard to the carbon atom labelled "*" (Scheme).

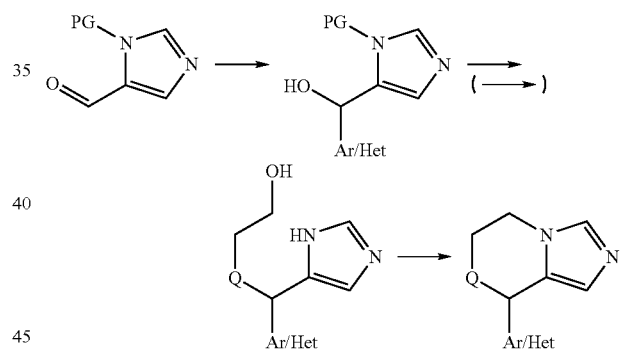

Details of the specific preparation variants can be found in the examples.

Separation into antipodes is possible by methods known per se, either, preferably, at an early stage in synthesis, by salt formation with an optically active acid such as, for example, (+)- or (−)-mandelic acid and separation of the diastereomeric salts by fractional crystallization, or, preferably, at a fairly late stage, by derivatization with a chiral auxiliary component, such as, for example, (+)- or (−)-camphanyl chloride and separation of the diastereomeric products by chromatography and/or crystallization and subsequent cleavage of the bond to the chiral auxiliary. The pure diastereomeric salts and derivatives can be analysed to determine the absolute configuration of the compound present, using customary spectroscopic methods, with single-crystal X-ray spectroscopy representing one particularly appropriate method.

Salts are primarily the pharmaceutically acceptable or non-toxic salts of compounds of the formula (I). Such salts are formed for example by compounds of the formula (I) containing an acidic group, such as a carboxyl or sulpho group and are, for example, salts thereof with suitable bases, such as non-toxic metal salts derived from metals of group Ia, Ib, IIa and IIb of the Periodic Table of the Elements, such as alkali metal salts, especially lithium, sodium or potassium salts, alkaline earth metal salts, magnesium or calcium salts for example, and also zinc salts or ammonium salts, and additionally salts formed with organic amines, such as unsubstituted or hydroxyl-substituted mono-, di- or trialkylamines, especially mono-, di- or tri-lower alkylamines, or with quaternary ammonium bases, e.g. methyl-, ethyl-, diethyl- or triethylamine, mono-, bis- or tris(2-hydroxyl-lower alkyl) amines, such as ethanolamine, diethanolamine or triethanolamine, tris(hydroxylmethyl)methylamine or 2-hydroxy-tertiary-butylamine, N,N-di-lower alkyl-N-(hydroxyl-lower alkyl)amine, such as N,N-di-N-dimethyl-N-(2-hydroxyl-ethyl)amine, or N-methyl-D-glucamine, or quaternary ammonium hydroxides, such as tetrabutylammonium hydroxide. The compounds of the formula (I) containing a basic group, such as an amino group, can form acid addition salts, with suitable inorganic acids for example, such as hydrohalic acid, such as hydrochloric acid, hydrobromic acid, or sulphuric acid with replacement of one or both protons, phosphoric acid with replacement of one or more protons, orthophosphoric acid or metaphosphoric acid for example, or pyrophosphoric acid with replacement of one or more protons, or with organic carboxylic, sulphonic or phosphonic acids or N-substituted sulphamic acids, e.g. acetic acid, propionic acid, glycolic acid, succinic acid, maleic acid, hydroxylmaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid, isonicotinic acid, and also amino acids, such as the α-amino acids specified earlier on, and also methanesulphonic acid, ethanesulphonic acid, 2-hydroxylethanesulphonic acid, ethane-1,2-disulphonic acid, benzenesulphonic acid, 4-toluenesulphonic acid, naphthalene-2-sulphonic acid, 2- or 3-phosphoglycerate, glucose 6-phosphate, N-cyclohexylsulphamic acid (to form cyclamates), or with other acidic organic compounds, such as ascorbic acid. Compounds of the formula (I) containing acidic and basic groups can also form inner salts.

Isolation and purification can also be carried out using pharmaceutically unsuitable salts.

The compounds of the formula (I) also include those compounds in which one or more atoms have been replaced by their stable, non-radioactive isotopes: for example, a hydrogen atom by deuterium.

Prodrug derivatives of the presently described compounds are derivatives thereof which when employed in vivo release the original compound as a result of a chemical or physiological process. A prodrug may be converted into the original compound, for example, when a physiological pH is reached or as a result of enzymatic conversion. Examples of possible prodrug derivatives include esters of freely available carboxylic acids, S- and O-acyl derivatives of thiols, alcohols or phenols, the acyl group being defined as above. Preference is given to pharmaceutically useful ester derivatives which are converted by solvolysis in physiological medium into the original carboxylic acid, such as, for example, lower alkyl esters, cycloalkyl esters, lower alkenyl esters, benzyl esters, mono- or disubstituted lower alkyl esters, such as lower ω-(amino, mono- or dialkylamino, carboxyl, lower alkoxycarbonyl)alkyl esters or such as lower α-(alkanoyloxy, alkoxycarbonyl or dialkylaminocarbonyl)alkyl esters; pivaloyloxymethyl esters and similar esters are conventionally used as ester derivatives of this kind.

Because of the close relationship between a free compound, a prodrug derivative and a salt compound, a defined compound in this invention also includes its prodrug derivative and salt form, insofar as this is possible and appropriate.

The naturally occuring estrogens 17β-estradiol (E2), estrone (E1) and estriol (E3) are C18 steroids derived from cholesterol. After binding to lipoprotein receptors, cholesterol is taken up by steroidogenic cells, stored and moved to the sites of steroid synthesis. Aromatization of the A-ring in the steroid scaffold is the last step in the formation of estrogen. This reaction is catalyzed by the P450 aromatase monooxygenase enzyme complex (Cyp19) that is present in the smooth endoplasmic reticulum and functions as a demethylase. In three consecutive hydroxylating reactions, estrone and estradiol are formed from their obligatory precursors androstenedione and testosterone, respectively.

The primary sources of estradiol in woman are the theca and granulose cells of the ovaries and the luteinized derivatives of these cells. According to the "two-cell" theory of estrogen synthesis, the theca cells secrete androgens that diffuse to the granulose cells to be aromatized to estrogens. There is, however, evidence that both cell types are enabled to form both androgens and estrogens. Estrone and estriol are primarily formed in the liver from estradiol. Aromatase activity has also been detected in muscle, fat, nervous tissue and the Leydig cells of the testes. The level of estrogen synthesis in extragonadal tissues increases as a function of age and body weight.

In the serum, estradiol reversibly binds to sex-hormone-binding globulin, a β-globulin, and with lesser affinity to albumin; about 2-3 percent is unbound. Estrogens are metabolized by sulfation or glucuronidation, and the conjugates are excreted into the bile or urine. Hydrolysis of these conjugates by the intestinal flora and subsequent reabsorption of the estrogens results in enterohepatic circulation.

Estrogens stimulate growth, blood flow and water retention in sexual organs and are also involved in causing breast cancer and endometrial tumors. In the liver, estrogens increase the expression of lipoprotein receptors that results in a decrease in serum concentrations of low-density lipoprotein cholesterol. Estrogens also increase the potential for coagulation by stimulating the production of coagulation factors in the liver. In bone, both osteoclasts and osteoblasts are direct targets of estrogens, but overall, estrogens are classified as anti-resorptive agents.

In breast tissue, estrogens stimulate the growth and differentiation of the ductal epithelium, induce mitotic activity of ductal cylindric cells and stimulate the growth of connective tissue. Estrogens stimulate the growth of breast cancer cells. In postmenopausal women with breast cancer, the tumor concentration of estradiol is high caused by in situ aromatization, despite the presence of low serum estradiol concentrations.

The compounds described in the present invention have useful pharmacological properties as they selectively inhibit the enzyme aromatase (Cyp19) in mammals, including humans. As a result, the metabolic conversion of androgens into estrogens is inhibited. The compounds are therefore suitable, for example, for the treatment of estrogen-dependent diseases, including estrogen-dependent breast cancer, particularly in postmenopausal women. They are also useful, for example, in the treatment of gynaecomastia, that is to say the development of breasts in men, as the aromatization of steroids can be inhibited by the described compounds.

These effects are demonstrable in in vitro assay tests using cell-free and cellular systems. The in vitro inhibition of aromatase activity of the compounds of the present invention can be demonstrated by using a commercial Cyp19 enzyme inhibition kit. The Cyp19/Methoxy-4-trifluoromethyl-coumarin (MFC) high throughput inhibition kit (Becton Dickinson Biosciences, San Jose, Calif., USA), for example, is designed to screen for potential inhibitors of Cyp19 catalytic activity in a 96-well format. The kit includes recombinant human Cyp19 enzyme in the form of supersomes, a fluorescent P450 substrate, an NADPH regenerating system, a reaction buffer and a stop reagent. MFC, the fluorogenic substrate is rapidly converted by Cyp19 supersomes to the highly fluorescent product 7-hydroxy-4-trifluoromethyl coumarin (7-HFC). The execution of the assay in the presence of various concentrations of inhibitor compounds ranging from 0.2 nanomolar to 20 millimolar occurs according to the manufacturer's instructions.

The inhibition curve is generated by fitting a 4-parameter logistic function to the raw data of the samples using the least squares approach. The function is described as follows:

$$Y=(d-a)/((1+(x/c)^{-b})+a)$$

with:
a=minimum data values
b=slope
c=$IC_{50}$
d=maximum data values
x=inhibitor concentrations The compounds described in the present invention show Cyp19 inhibitory properties at minimal concentrations between $10^{-3}$ to $10^{-10}$ mol/l.

Example of CYP19 Inhibition:

| Example number | IC50 value [nM] |
| --- | --- |
| 1 | 7.1 |
| antipode of 1 | 2769.0 |

The Cyp19 inhibitory properties of compounds described in the present invention can also be demonstrated in a cellular assay. The NCI-H295R human adrenocortical carcinoma cell line has been characterized in detail in the literature and shown to express most of the key enzymes necessary for steroidogenesis. These include Cyp11A (cholesterol side-chain cleavage), Cyp11B1 (steroid 11β-hydroxylase), Cyp11B2 (aldosterone synthetase), Cyp17 (steroid 17α-hydroxylase and/or 17,20 lyase), Cyp19 (aromatase), Cyp21B2 (steroid 21-hydroxylase) and 3β-HSD (hydroxysteroid dehydrogenase). The cells have the physiological characteristics of zonally undifferentiated human fetal adrenal cells, with the ability to produce the steroid hormones of each of the three phenotypically distinct zones found in the adult adrenal cortex.

The NCI-H295R cells (American Type Culture Collection, ATCC, Rockville, Md., USA) are cultured in Dulbecco's Modified Eagle'Ham F-12 medium (DME/F12) that is supplemented with Ultroser SF serum (Soprachem, Cergy-Saint-Christophe, France) as well as insulin, transferrin, selenit (I-T-S, Becton Dickinson Biosiences, Franklin Lakes, N.J., USA) and antibiotics in 75 cm² cell culture flasks at a temperature of 37° C. and a 95% air/5% $CO_2$ humidified atmosphere. The cells are subsequently transferred in a 24-well plate and seeded in presence of DME/F12 medium that is supplemented with 0.1% bovine serum albumin instead of Ultroser SF serum. The experiment is initiated by incubating the cells for 72 hours in DME/F12 medium supplemented with 0.1% bovine serum albumin and test compounds in the presence or absence of cell stimulatory agents. The test compound is added in a concentration range of 0.2 nanomolar to 20 millimolar. As cell-stimulatory agents, angiotensin-II (at 10 or 100 nanomolar concentration), potassium ions (at 16 millimolar), forskolin (at 10 micromolar) or a combination of two agents are used. The cellular secretion of estrone, estradiol, dihydroepiandrostendione, aldosterone, corticosterone and/or cortisol into the cell culture medium can be quantitatively assessed with commercially available immuno-assays and specific monoclonal antibodies according to the manufacturer's instructions. The degree of secretion of a selective steroid is used as a measure of enzyme activity, respectively enzyme inhibition in the presence of absence of a test compound. The dose-dependent enzyme inhibitory activity of a compound is reflected in a inhibition curve that is characterized by an $IC_{50}$ value.

The inhibition curve is generated by fitting a 4-parameter logistic function to the raw data of the samples using the least squares approach. The function is described as follows:

$$Y=(d-a)/((1+(x/c)^{-b})+a)$$

with:
a=minimum data values
b=slope
c=$IC_{50}$
d=maximum data values
x=inhibitor concentrations The compounds described in the present invention show Cyp19 inhibitory properties at minimal concentrations between $10^{-3}$ to $10^{-10}$ mol/l.

The aromatase inhibitory effects of described compounds can be also demonstrated in vivo using advantageously mammalian animal models such as e.g. guinea pigs, mice, rats, cats, dogs, or monkeys.

The compound-mediated in vivo inhibition of aromatase activity can be tested by monitoring plasma steroid level changes as described in the following protocol: cycling female rats are injected subcutaneously 5-times on alternate days with 100 IU of pregnant mare's serum gonadotropin (PMSG, Sigma) in 0.1 ml sterile saline. Twenty-four hours after the last injection, the animals are treated orally with test compound at doses ranging from 0.01 to 10 mg/kg. Twenty-four hours after treatment, the animals are subjected to a terminal bleed. Heparinized plasma is stored at −20° C. until analysis. Plasma levels of steroid (17beta-estradiol, estrone, estriol, progesterone, testosterone, aldosterone and corticosterone) are determined by commercially available radioimmunoassay kits, according to the manufacturer's instructions. A purification and concentration step is needed to measure plasma testosterone in female rats: four volumes of diethyl ether are added to the samples, mixed by gentle inversion for 15 minutes and then centrifuged for 5 minutes at 2000 rpm. The aqueous phase is frozen in dry ice and the organic phase is recovered and evaporated to dryness under a nitrogen stream. The dried extract is reconstituted in the assay buffer.

The compound-mediated in vivo inhibition of aromatase activity can be tested by monitoring the ovary estrogen content as follows: twenty-one day old female rats are injected subcutaneously with 10 IU pregnant mare serum gonadotropin (PMSG, Sigma). Two days later, the same rats are injected subcutaneously with 30 IU human chorionic gonadotropin (hCG, Sigma). On the day following the hCG treatment, the rats are injected subcutaneously with either propylene glycol (0.2 ml) or with various doses of the test compound. One hour later, all the rats are treated with 2.25 mg 4-androstene-3,17-dione in 0.1 ml oil, subcutaneously. Four hours after the injection of androstenedione, the rats are killed and their ovaries removed and trimmed free of adhering tissue and stored in pairs at −50° C. To determine the total estrogen content of the ovaries, 1.5 ml of 0.05 M aqueous potassium phosphate buffer (pH 7.4) and 0.2 ml of 0.1 N aqueous NaOH are added to the tissues which are then homogenized. The homogenate is extracted with 15 ml of diethyl ether. 5 ml aliquots are radioimmunoassayed with antiserum having 100% cross-reactivity with estrone, estradiol and estriol. The results are expressed as ng estrogen/pair of ovaries.

The anti-tumor activity, especially in estrogen-dependent tumors, can be demonstrated in vivo e.g. in dimethylbenzanthracene (DMBA)-induced mammary tumors in female Sprague-Dawley rats (see Proc. Soc. Exp. Biol. Med. 160, 296-301, 1979). Compounds of the invention cause regression of existing tumors and suppress the appearance of new tumors at daily doses of about 1 to about 20 mg/kg p.o or less.

In order to achieve the desired effects in a patient to be treated, the compounds of the present invention can be administered orally or enterally, such as, for example, intravenously, intraperitoneally, intramuscularly, rectally, subcutaneously or else by direct injection of the active substance locally into tissues or tumours. The term patient encompasses warm-blooded species and mammals such as, for example, human, primate, bovine, dog, cat, horse, sheep, mouse, rat and pig. The compounds can be administered as pharmaceutical product or be incorporated into an administration device which ensures sustained release of the compound. The amount of substance to be administered can vary over a wide range and represent every effective dose. Depending on the patient to be treated or the condition to be treated and mode of administration, the dose of the effective substance each day can be between about 0.005 and 50 milligrams per kilogram of body weight, but is preferably between about 0.05 and 5 milligrams per kilogram of body weight each day.

For oral administration, the compounds can be formulated in solid or liquid pharmaceutical forms such as, for example, as capsules, pills, tablets, coated tablets, granules, powders, solutions, suspensions or emulsions. The dose of a solid pharmaceutical form can be one usual hard gelatine capsule which may be filled with active ingredients and excipients such as lubricants and fillers, such as, for example, lactose, sucrose and maize starch. Another form of administration may be represented by tableting of the active substance of the present invention. The tableting can take place with conventional tableting excipients such as, for example, lactose, sucrose, maize starch, combined with binder from gum acacia, maize starch or gelatine, disintegrants such as potato starch or crosslinked polyvinylpyrrolidone (PVPP) and lubricants such as stearic acid or magnesium stearate.

Examples of excipients suitable for soft gelatine capsules are vegetable oils, waxes, fats, semisolid and liquid polyols etc.

Examples of excipients suitable for producing solutions and syrups are water, polyols, sucrose, invert sugar, glucose etc.

For rectal administration, the compounds can be formulated in solid or liquid pharmaceutical forms such as, for example, suppositories. Examples of excipients suitable for suppositories are natural or hardened oils, waxes, fats, semi-liquid or liquid polyols etc.

For parenteral administration, the compounds can be formulated as injectable dosage of the active ingredient in a liquid or suspension. The preparations usually comprise a physiologically tolerated sterile solvent which may comprise a water-in-oil emulsion, with or without surfactant, and other pharmaceutically acceptable excipients. Oils which can be used for such preparations are paraffins and triglycerides of vegetable, animal or synthetic origin, such as, for example, peanut oil, soya oil and mineral oil. Injectable solutions generally comprise liquid carriers such as, preferably, water, saline, dextrose or related sugar solutions, ethanol and glycols such as propylene glycol or polyethylene glycol.

The substances may be administered as transdermal patch system, as depot injection or implant if the formulation makes sustained delivery of the active ingredient possible. The active substance can be compressed as granules or to narrow cylinders and be administered subcutaneously or intramuscularly as depot injection or implant.

The pharmaceutical products may in addition also comprise preservatives, solubilizers, viscosity-increasing substances, stabilizers, wetting agents, emulsifiers, sweeteners, colorants, aromatizing agents, salts to change the osmotic pressure, buffers, coating agents or antioxidants. They may also comprise other therapeutically valuable substances too.

The present invention further provides the use of the compounds of the formula (I) and the pharmaceutically acceptable salts thereof in the treatment or prevention of a disease or conditions which responds to aromatase inhibition, in particular a proliferative disease such as breast cancer or similar soft tissue endocrine-sensitive cancer, most preferably estrogen -dependent conditions like gynecomastia, mammary and endometrial tumors, endometrioisis and premature labor. The compounds are also useful for the treatment or prevention of locally advanced or metastatic breast cancer in postmenopausal women with hormone receptor positive or unknown.

The compounds of the formula (I) and the pharmaceutically acceptable salts thereof may also be administered in combination with one or more agents having anti-neoplastic actions, such as anti-oestrogenic activity as described for example for exemestane, toremifene, fulvestrant, tamoxifen; such as bone resorption inhibititory activity as described for example for pamidronate, zoledronic acid, such as alkylating activity as described for busulfan, temozolomide, melphalan, chlorambucil, mechlorethalamine, such as nucleotide base intercalating activity as described for example for adriamycin, daunorubicin, dactinomcyin, doxorubicin, epirubicin, idarubicin; such as anti-metabolite activity as described for example for cytarabine, fludarabine, cladrbine, mercaptopurine, thioguanine, capecitabine; such as anti-androgenic activity as described for example for abarelix, bicalutamide; such as androgenic activity as described for example for nilutamide, methyltestosterone; such as gonadotropin releasing hormone activity as described for example for leuprolide, triptorelin, goserelin; such as progestogenic activity as described for example for medroxyprogesterone, such as nucleoside analogue activity as described for example for gemcitarabine; such as topoisomerase I inhibitory activity as described for example for topotecan, irinotecan; such as kinase inhibitory activity as described for example for imatinib; such as growth factor inhibitory activity as described for example for gefitinib, trastuzumab; such as growth hormone activity as described for example for epoetin alfa, sargramostim, filgastrim, pegfilgastrim, oprelvekin, interferon alpha 2b; such as miscellaneous anti-tumor activity as described for example for pemetrexed, dacarbazine, procarbazine, oxaliplatin, asparaginase, pegaspargase, altetamine, gemtuzumab, vinorelbine, mitoxantrone, denileukin, rituximab, alitretinoin, arsenic trioxide, bortezomib, tretinoin, docetaxel; such as antiemetic activity as described for example for dolasetron, palonosetron, aprepitant, ganisetron, dronabinol, odansetron.

The compounds described in the present invention may be used as follows:

As therapeutic combination in form of a preparation or a kit that is composed of individual components, including a herein described compound of the formula (I) and the pharmaceutically usable salts thereof and at least one medication with anti-neoplastic activity that can be administered either simultaneously or sequentially. The preparation or the kit may contain instructions of usage.

The dose may vary within wide limits and has of course to be adapted to the individual circumstances in each individual case. In general, for oral administration, a daily dose of about 0.3 mg to about 3 g, preferably about 1 mg to about 1 g, for example about 10 mg, per adult (70 kg), divided into preferably 1-3 individual doses which may, for example, be of equal size, may be appropriate, although the upper limit specified may also be exceeded if this should be found to be appropriate; typically, children receive a lower dose according to their age and body weight.

EXAMPLES

The following examples illustrate the present invention. All temperatures are stated in degrees Celsius, pressures in mbar. Unless mentioned otherwise, the reactions take place at room temperature. The abbreviation "Rf=xx(A)" means for example that the Rf is found in solvent system A to have the value xx. The proportion of solvents to one another is always stated in fractions by volume. Chemical names of end products and intermediates were generated with the aid of the AutoNom 2000 (Automatic Nomenclature) program.

HPLC gradient on Hypersil BDS C-18 (5 µm); column: 4×125 mm:
  90% water*/10% acetonitrile* to 0% water*/100% acetonitrile* in 5 minutes +2.5 minutes (1.5 ml/min)

* contains 0.1% trifluoroacetic acid

The abbreviations used are as follows:

Rf ratio of distance travelled by a substance to distance of the eluent from the starting point in thin-layer chromatography
Rt retention time of a substance in HPLC (in minutes)
m.p. melting point (temperature)

1

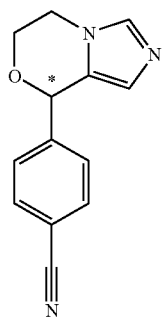

-continued

2

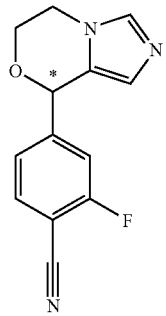

3

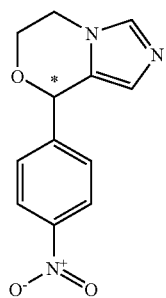

4

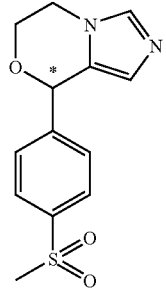

5

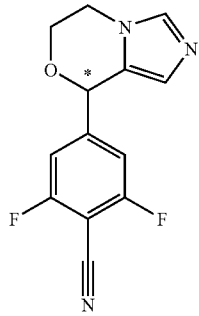

6

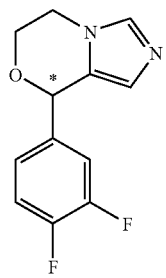

-continued

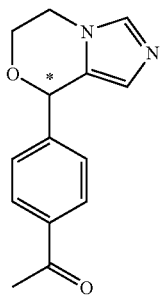
7

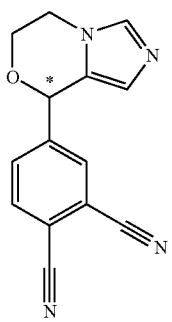
8

Example 1

4-(5,6-Dihydro-8H-imidazo[5,1-c][1,4]oxazin-8-yl)benzonitrile

A solution of 1.20 mmol of 2-[(4-cyanophenyl)-(3H-imidazol-4-yl)methoxy]ethyl methanesulphonate in 10 ml of acetonitrile is heated to reflux for 24 hours. The reaction mixture is cooled to room temperature and evaporated. The title compound is obtained as a white solid from the residue by flash chromatography (SiO$_2$ 60F). Rf=0.14 (dichloromethane -2M ammonia in ethanol 95:5); Rt=4.29.

The starting materials are prepared as follows:

a) 2-[(4-Cyanophenyl)-(3H-imidazol-4-yl)methoxy]ethyl methanesulphonate 1.44 mmol of diisopropylethylamine and 1.20 mmol of methanesulphonyl chloride are added to a solution of 1.20 mmol of 4-[(2-hydroxyethoxy)-(3H-imidazol-4-yl)methyl] benzonitrile in 10 ml of dichloromethane at 0° C. The reaction mixture is stirred at 0° C. for 3 hours, tipped into water and extracted with dichloromethane. The combined organic phases are washed with brine, dried over sodium sulphate and evaporated. The crude title compound is used without further purification in the next stage.

b) 4-[(2-Hydroxyethoxy)-(3H-imidazol-4-yl)methyl]benzonitrile 2.45 mmol of sodium borohydride are added to a solution of 1.63 mmol of ethyl [(4-cyanophenyl)-1-(trityl-1H-imidazol-4-yl)methoxy]acetate in 10 ml of ethanol at room temperature. The reaction mixture is stirred at room temperature for 16 hours and then evaporated. The residue is taken up in dichloromethane and saturated aqueous sodium bicarbonate solution, the phases are separated, and the aqueous phase is back-extracted with dichloromethane. The combined organic phases are dried with sodium sulphate and evaporated. The title compound is obtained as a white solid from the residue by flash chromatography (SiO$_2$ 60F). Rf=0.10 (ethyl acetate-heptane 1:2); Rt=7.39.

c) Ethyl [(4-cyanophenyl)-(1-trityl-1H-imidazol-4-yl)methoxy]acetate 5.00 mmol of 4-[hydroxy-(1-trityl-1H-imidazol-4-yl)methyl]benzonitrile are added to a mixture of 6.50 mmol of sodium hydride (60% dispersion in paraffin) in 20 ml of N,N-dimethylformamide at 0° C. The reaction mixture is stirred at 0° C. for 1 hour and then bromoacetic acid is added dropwise. The reaction mixture is stirred at room temperature for 16 hours, poured into water and extracted with tert-butyl methyl ether. The combined organic phases are washed with brine, dried with sodium sulphate and evaporated. The title compound is obtained as an amber-coloured oil from the residue by flash chromatography (SiO$_2$ 60F). Rf=0.42 (ethyl acetate-heptane 1:2); Rt=8.00.

d) 4-[Hydroxy-(1-trityl-1H-imidazol-4-yl)methyl]benzonitrile

A solution of 14.80 mmol of 4-iodobenzonitrile [3058-39-7] in 20 ml of tetrahydrofuran is cooled to −30° C., and 14.80 mmol of i-propylmagnesium chloride (2M in tetrahydrofuran) are added. The mixture is stirred at −30° C. for 60 minutes and a solution, precooled to −30° C., of 11.84 mmol of 1-trityl-1H-imidazole-4-carbaldehyde [33016-47-6] in 30 ml of tetrahydrofuran is added. The mixture is stirred at −30° C. for 30 minutes, and then the reaction mixture is warmed to room temperature and quenched with saturated aqueous ammonium chloride solution. The phases are separated, and the aqueous phase is extracted with ethyl acetate (3×). The combined organic phases are washed with brine, dried with magnesium sulphate and evaporated. The title compound is obtained as a white solid from the residue by recrystallization from ethyl acetate. Rf=0.23 (CH$_2$Cl$_2$ 2M NH$_3$ in EtOH 97:3); Rt=7.32.

The racemic compound is fractionated into the enantiomers by chiral preparative HPLC to afford the title compound. The title compound is isolated as the enantiomer which elutes first. Rt*=5.41 min.

* HPLC Method:

Column: 250×50 mm CHIRALPAK® AD 20 μm

Mobile phase: CO$_2$/methanol 80:20

Flow rate: 240 ml/min

Detection: UV 250 nm

Temperature: 25° C.

Pressure: 150 bar

The following compounds are prepared in analogy to the process described in Example 1:

2 4-(5,6-Dihydro-8H-imidazo[5,1-c][1,4]oxazin-8-yl)-2-fluorobenzonitrile starting from 2-fluoro-4-iodobenzonitrile [137553-42-5].

3 8-(4-Nitrophenyl)-5,6-dihydro-8H-imidazo[5,1-c][1,4]oxazine starting from 1-iodo-4-nitrobenzene [636-98-6]. Tetrahydrofuran is used instead of N,N-dimethylformamide as solvent in stage c 4 8-(4-Methanesulphonylphenyl)-5,6-dihydro-8H-imidazo[5,1-c][1,4]oxazine starting from 1-iodo-4-methanesulphonylbenzene [64984-08-3].

5 4-(5,6-Dihydro-8H-imidazo[5,1-c][1,4]oxazin-8-yl)-2,6-difluorobenzonitrile starting from 2,6-difluoro-4-iodobenzonitrile [14743-50-3].

6 8-(3,4-Difluorophenyl)-5,6-dihydro-8H-imidazo[5,1-c][1,4]oxazine starting from 3,4-difluoro-1-iodobenzene [64248-58-4]. White wax.

8 4-(5,6-Dihydro-8H-imidazo[5,1-c][1,4]oxazin-8-yl)phthalonitrile starting from 4-iodophthalonitrile [69518-17-8].

Example 7

1-[4-(5,6-Dihydro-8H-imidazo[5,1-c][1,4]oxazin-8-yl)phenyl]ethanone 3 mmol of methylmagnesium bromide solution (3M in diethyl ether) are added to a solution of 0.97 mmol of 4-(5,6-dihydro-8H-imidazo[5,1-c][1,4]oxazin-8-yl)-N-methoxy-N-methylbenzamide in 10 ml of absolute tetrahydrofuran under argon. The reaction solution is stirred at room temperature for 4 hours and then poured into saturated aqueous ammonium chloride solution and extracted with tert-butyl methyl ether. The combined organic phases are dried over magnesium sulphate and evaporated. The title compound is obtained as a beige solid from the residue by flash chromatography (SiO$_2$ 60F).

Rf=0.19 (dichloromethane-2M ammonia in ethanol 97:3); Rt=4.10.

The starting materials are prepared as follows:

a) 4-(5,6-Dihydro-8H-imidazo[5,1-c][1,4]oxazin-8-yl)-N-methoxy-N-methylbenzamide 9.30 mmol of thionyl chloride are added to a solution of 3.10 mmol of 4-(5,6-dihydro-8H-imidazo[5,1-c][1,4]oxazin-8-yl)benzoic acid in 5 ml of chloroform. The reaction mixture is heated to reflux for 3 hours and then evaporated. The residue is stripped with toluene and then taken up in 10 ml of dichloromethane. The reaction solution is cooled to 0-5° C., and 3.10 mmol of N,O-dimethylhydroxylamine hydrochloride, followed by 15.5 mmol of diisopropylethylamine, are added. The reaction mixture is stirred at room temperature for 16 hours and filtered through Hyflo, and the filtrate is evaporated. The title compound is obtained as a yellowish oil from the residue by flash chromatography (SiO$_2$ 60F). Rf=0.13 (dichloromethane-2M ammonia in ethanol 97:3); Rt=4.00.

b) 4-(5,6-Dihydro-8H-imidazo[5,1-c][1,4]oxazin-8-yl)benzoic acid

A solution of 3.10 mmol of 4-(5,6-dihydro-8H-imidazo[5,1-c][1,4]oxazin-8-yl)benzonitrile (Example 1) in 5 ml of ethanol is mixed with 3.1 ml of 2M sodium hydroxide solution. The reaction solution is heated to reflux for 24 hours. The reaction mixture is cooled to room temperature, neutralized with 2M hydrochloric acid and evaporated. The crude product is employed without further purification for the next stage. Rt=3.79.

The invention claimed is:

1. A compound of the formula

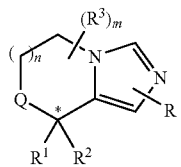

(I)

in which

R is deuterium, halogen, or hydrogen;

R$^1$ is aryl-C$_0$-C$_4$-alkyl or heterocyclyl-C$_0$-C$_4$-alkyl, which radicals are unsubstituted or substituted by 1-4 C$_1$-C$_8$ alkoxy, C$_1$-C$_8$ alkoxycarbonyl, C$_1$-C$_8$ alkyl, C$_0$-C$_8$ alkylcarbonyl, C$_1$-C$_8$ alkylsulphonyl, unsubstituted or substituted aryl, aryl-C$_0$-C$_4$ alkoxycarbonyl, cyano, halogen, unsubstituted or substituted heterocyclyl, hydroxy, nitro, oxide, oxo, tri-C$_1$-C$_4$ alkylsilyl, trifluoromethoxy or trifluoromethyl, wherein the heterocyclyl of the heterocyclyl-C$_0$-C$_4$-alkyl stands for a saturated, partially saturated or unsaturated, 4-8-membered monocyclic ring system, or a saturated, partially saturated or unsaturated, 7-12-membered bicyclic ring system, or a partially saturated or unsaturated, 9-12-membered tricyclic ring system which comprises an N, O or S atom in at least one of the rings, it being possible for an additional N, O or S atom to be present in one ring;

R$^2$ is a) deuterium, halogen, hydroxy, cyano or hydrogen; or b) C$_2$-C$_8$ alkenyl, C$_2$-C$_8$ alkynyl, C$_1$-C$_8$ alkoxy, C$_1$-C$_4$ alkoxycarbonyl-C$_1$-C$_4$ alkyl, C$_1$-C$_8$ alkyl, C$_0$-C$_4$ alkylcarbonyl, aryl-C$_0$-C$_4$ alkyl, carboxy-C$_1$-C$_4$ alkyl, C$_3$-C$_8$ cycloalkyl or heterocyclyl-C$_0$-C$_4$ alkyl, which radicals are unsubstituted or substituted by 1-4 C$_1$-C$_8$ alkoxy, C$_1$-C$_8$ alkoxycarbonyl, C$_1$-C$_8$ alkyl, C$_0$-C$_8$ alkylcarbonyl, C$_1$-C$_8$ alkylsulphonyl, unsubstituted or substituted aryl, aryl-C$_0$-C$_4$ alkoxycarbonyl, cyano, halogen, unsubstituted or substituted heterocyclyl, hydroxy, nitro, oxide, oxo, tri-C$_1$-C$_4$ alkylsilyl, trifluoromethoxy or trifluoromethyl;

R$^3$ is C$_1$-C$_8$ alkyl;

Q is oxygen;

m is a number 0, 1 or 2;

n is 1;

or a pharmaceutically acceptable salt thereof, where

R$^1$ is not C$_1$-C$_8$ alkyl-substituted aryl if R$^2$ is hydrogen, and which compound shows an aromatase inhibitory activity at least 10 times higher, than the compound of the formula (I) with the opposite configuration around the asymmetric carbon atom labelled "*".

2. A compound according to claim 1, where R is deuterium or hydrogen.

3. A compound according to claim 1, where R$^1$ is optionally substituted phenyl, optionally substituted naphthyl, benzofuranyl, benzo[b]thiophenyl, benzoimidazolyl, benzo[d]isothiazolyl, benzo[d]isoxazolyl, benzo[b]thiophenyl, imidazolyl, indazolyl, oxazolyl, pyridyl, pyrrolyl, thiazolyl or thiophenyl.

4. A compound according to claim 1, where R$^2$ is C$_1$-C$_8$ alkoxy, hydroxy, C$_1$-C$_8$ alkyl, optionally substituted aryl-C$_0$-C$_4$ alkyl, deuterium, halogen, cyano or hydrogen.

5. A method for the treatment of estrogen-dependent breast cancer, which comprises administering to a subject having the disease a therapeutically effective amount of a compound of the formula (I) or a pharmaceutically acceptable salt thereof according to claim 1.

6. A method for the treatment of gynaecomastia, which comprises administering to a subject having gynaecomastia a therapeutically effective amount of a compound of the formula (I) or a pharmaceutically acceptable salt thereof according to claim 1.

7. A pharmaceutical composition comprising a compound of formula (I) or a pharmaceutically acceptable salt thereof according to claim 1, and a pharmaceutically acceptable excipient.

* * * * *